United States Patent
Lee et al.

(10) Patent No.: US 9,358,067 B2
(45) Date of Patent: Jun. 7, 2016

(54) TISSUE ABLATION SYSTEM WITH INTERNAL AND EXTERNAL RADIATION SOURCES

(71) Applicant: COVIDIEN LP, Mansfield, MA (US)

(72) Inventors: Anthony C. Lee, San Francisco, CA (US); Joseph D. Brannan, Erie, CO (US); Mani N. Prakash, Boulder, CO (US); Francesca Rossetto, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 296 days.

(21) Appl. No.: 13/889,989

(22) Filed: May 8, 2013

(65) Prior Publication Data
US 2013/0253500 A1   Sep. 26, 2013

Related U.S. Application Data

(62) Division of application No. 12/713,641, filed on Feb. 26, 2010, now abandoned.

(51) Int. Cl.
*A61B 18/18* (2006.01)

(52) U.S. Cl.
CPC ..... *A61B 18/1815* (2013.01); *A61B 2018/1869* (2013.01)

(58) Field of Classification Search
CPC ................... A61B 18/1815; A61B 2018/1838; A61B 2018/1869
USPC ...................................... 606/33; 607/101, 156
See application file for complete search history.

(56) References Cited

U.S. PATENT DOCUMENTS

| D263,020 S | 2/1982 | Rau, III |
| D295,893 S | 5/1988 | Sharkany et al. |
| D295,894 S | 5/1988 | Sharkany et al. |

(Continued)

FOREIGN PATENT DOCUMENTS

| CN | 1103807 | 6/1995 |
| DE | 390937 | 3/1924 |

(Continued)

OTHER PUBLICATIONS

Johnson et al., "New Low-Profile Applicators for Local Heating of Tissues", IEEE Transactions on Biomedical Engineering, vol. BME-31, No. 1, Jan. 1984, pp. 28-37.

(Continued)

*Primary Examiner* — Michael Peffley
*Assistant Examiner* — Thomas Giuliani

(57) ABSTRACT

According to one embodiment of the present disclosure a microwave ablation system is disclosed. The microwave ablation system includes an energy source adapted to generate microwave energy and a plurality of energy delivery devices having a first energy delivery device configured to be inserted into tissue and to generate a non-directional ablation volume and a second energy delivery device configured to be positioned relative to the tissue and to generate a directional ablation volume. The system also includes a power dividing device having an input adapted to connect to the energy source and a plurality of outputs configured to be coupled to the plurality of energy delivery devices. The power dividing device is configured to selectively divide energy provided from the energy source between the plurality of energy delivery devices.

7 Claims, 5 Drawing Sheets

(56) References Cited

U.S. PATENT DOCUMENTS

| | | | |
|---|---|---|---|
| D424,694 S | 5/2000 | Tetzlaff et al. | |
| D425,201 S | 5/2000 | Tetzlaff et al. | |
| 6,277,113 B1 | 8/2001 | Berube | |
| 6,278,411 B1* | 8/2001 | Ohlsson | G01F 23/284 343/772 |
| 6,287,302 B1* | 9/2001 | Berube | 606/33 |
| D449,886 S | 10/2001 | Tetzlaff et al. | |
| 6,312,427 B1 | 11/2001 | Berube et al. | |
| 6,364,876 B1 | 4/2002 | Erb et al. | |
| D457,958 S | 5/2002 | Dycus et al. | |
| D457,959 S | 5/2002 | Tetzlaff et al. | |
| 6,527,768 B2 | 3/2003 | Berube | |
| 6,652,515 B1 | 11/2003 | Maguire et al. | |
| D496,997 S | 10/2004 | Dycus et al. | |
| D499,181 S | 11/2004 | Dycus et al. | |
| 6,823,218 B2 | 11/2004 | Berube | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,278,991 B2 | 10/2007 | Morris et al. | |
| 7,326,201 B2 | 2/2008 | Fjield et al. | |
| D564,662 S | 3/2008 | Moses et al. | |
| 7,354,436 B2 | 4/2008 | Rioux et al. | |
| 7,422,586 B2 | 9/2008 | Morris et al. | |
| 2002/0087151 A1 | 7/2002 | Mody et al. | |
| 2006/0282069 A1 | 12/2006 | Prakash et al. | |
| 2007/0198006 A1 | 8/2007 | Prakash et al. | |
| 2008/0147056 A1* | 6/2008 | van der Weide et al. | 606/33 |
| 2008/0269851 A1* | 10/2008 | Deem | A61B 18/18 607/101 |
| 2009/0326620 A1 | 12/2009 | Rossetto et al. | |
| 2010/0049178 A1* | 2/2010 | Deem | A61B 18/02 606/9 |
| 2011/0213353 A1* | 9/2011 | Lee et al. | 606/33 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 00/36985 | 6/2000 |
| WO | WO 2010/035831 | 4/2010 |

OTHER PUBLICATIONS

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/483,742, filed Jun. 7, 1995, Roger A. Stern.
U.S. Appl. No. 08/136,098, filed Oct. 14, 1993, Roger A. Stern.
U.S. Appl. No. 12/199,935, filed Aug. 28, 2008, Robert A. Willyard.
U.S. Appl. No. 12/203,474, filed Sep. 3, 2008, Robert J. Behnke.
U.S. Appl. No. 12/236,686, filed Sep. 24, 2008, Ronald J. Podhajsky.
U.S. Appl. No. 12/244,850, filed Oct. 3, 2008, Joseph A. Paulus.
U.S. Appl. No. 12/250,110, filed Oct. 13, 2008, Frencesca Rossetto.
U.S. Appl. No. 12/250,171, filed Oct. 13, 2008, Francesca Rossetto.
U.S. Appl. No. 12/251,857, filed Oct. 15, 2008, Anna Belous.
U.S. Appl. No. 12/253,457, filed Oct. 17, 2008, Joseph D. Brannan.
U.S. Appl. No. 12/389,906, filed Feb. 20, 2009, Francesca Rossetto.
U.S. Appl. No. 12/389,915, filed Feb. 20, 2009, Francesca Rossetto.
U.S. Appl. No. 12/401,268, filed Mar. 10, 2009, Ian Smith.
U.S. Appl. No. 12/416,583, filed Apr. 1, 2009, Joseph D. Brannan.
U.S. Appl. No. 12/419,395, filed Apr. 7, 2009, Mani Prakash.
U.S. Appl. No. 12/423,609, filed Apr. 14, 2009, Jeffrey L. Jensen.
U.S. Appl. No. 12/436,237, filed May 6, 2009, Ronald J. Podhajsky.
U.S. Appl. No. 12/436,239, filed May 6, 2009, Ronald J. Podhajsky.
U.S. Appl. No. 12/436,231, filed May 6, 2009, Ronald J. Podhajsky.

(56) References Cited

OTHER PUBLICATIONS

U.S. Appl. No. 12/472,831, filed May 27, 2009, Joseph D. Brannan.
U.S. Appl. No. 12/475,082, filed May 29, 2009, Darion Peterson.
U.S. Appl. No. 12/476,960, filed Jun. 2, 2009, Mani N. Prakash.
U.S. Appl. No. 12/487,917, filed Jun. 19, 2009, Joseph D. Brannan.
U.S. Appl. No. 12/493,302, filed Jun. 29, 2009, Darion Peterson.
U.S. Appl. No. 12/504,738, filed Jul. 17, 2009, Robert J. Behnke.
U.S. Appl. No. 12/535,851, filed Aug. 5, 2009, Joseph D. Brannan.
U.S. Appl. No. 12/535,856, filed Aug. 5, 2009, Joseph D. Brannan.
U.S. Appl. No. 12/536,616, filed Aug. 6, 2009, Arnold V. DeCarlo.
U.S. Appl. No. 12/542,348, filed Aug. 17, 2009, Joseph D. Brannan.
U.S. Appl. No. 12/542,785, filed Aug. 18, 2009, Joseph D. Brannan.
U.S. Appl. No. 12/547,155, filed Aug. 25, 2009, Robert J. Behnke.
U.S. Appl. No. 12/548,644, filed Aug. 27, 2009, Darion Peterson.
U.S. Appl. No. 12/555,576, filed Sep. 8, 2009, Kenlyn S. Bonn.
U.S. Appl. No. 12/556,010, filed Sep. 9, 2009, Ian S. Smith.
U.S. Appl. No. 12/561,096, filed Sep. 16, 2009, Kenlyn S. Bonn.
U.S. Appl. No. 12/562,575, filed Sep. 18, 2009, Joseph D. Brannan.
U.S. Appl. No. 12/562,842, filed Sep. 18, 2009, Robert J. Behnke, II.
U.S. Appl. No. 12/566,299, filed Sep. 24, 2009, Richard A. Willyard.
U.S. Appl. No. 12/568,067, filed Sep. 28, 2009, Francesca Rossetto.
U.S. Appl. No. 12/568,524, filed Sep. 28, 2009, Kenlyn S. Bonn.
U.S. Appl. No. 12/568,551, filed Sep. 28, 2009, Joseph D. Brannan.
U.S. Appl. No. 12/568,777, filed Sep. 29, 2009, Kenlyn S. Bonn.
U.S. Appl. No. 12/568,838, filed Sep. 29, 2009, Kenlyn S. Bonn.
U.S. Appl. No. 12/568,883, filed Sep. 29, 2009, Joseph D. Brannan.
U.S. Appl. No. 12/568,972, filed Sep. 29, 2009, Joseph D. Brannan.
U.S. Appl. No. 12/569,171, filed Sep. 29, 2009, Joseph D. Brannan.
U.S. Appl. No. 12/569,685, filed Sep. 29, 2009, Joseph D. Brannan.
U.S. Appl. No. 12/582,857, filed Oct. 21, 2009, Charles D. Allen.
U.S. Appl. No. 12/606,769, filed Oct. 27, 2009, Joseph D. Brannan.
U.S. Appl. No. 12/607,221, filed Oct. 28, 2009, Joseph D. Brannan.
U.S. Appl. No. 12/607,268, filed Oct. 28, 2009, Joseph D. Brannan.
U.S. Appl. No. 12/619,462, filed Nov. 16, 2009, Casey M. Ladtkow.
U.S. Appl. No. 12/620,289, filed Nov. 17, 2009, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.

Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical lmpedence" Am. J. MI, Jan. Mar. 1964, pp. 16-27.
Goldberg et al., "Image-guided Radiofrequency Tumor Ablation: Challenges and Opportunities—Part I", (2001) J Vasc. lnterv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).

(56) References Cited

OTHER PUBLICATIONS

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" Anz Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology "Overcoming the Challenge" located at: <http://www.urologix.com-!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP" Neurosurgical Review 7:2-3 (1984) pp. 187-190.

(56) References Cited

OTHER PUBLICATIONS

W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report Ep 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
European Search Report EP 09172838.6 extended dated Jan. 20, 2010.
European Search Report EP 09173268.5 extended dated Jan. 27, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.

(56) References Cited

OTHER PUBLICATIONS

International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

TISSUE ABLATION SYSTEM WITH INTERNAL AND EXTERNAL RADIATION SOURCES

The present application is a divisional application, which claims priority to, and the benefit of, U.S. patent application Ser. No. 12/713,641, filed on Feb. 26, 2010, the disclosure of which is herein incorporated by reference in its entirety.

BACKGROUND

1. Technical Field

The present disclosure relates to apparatus and methods for providing energy to tissue and, more particularly, to devices and electromagnetic radiation delivery procedures utilizing ablation probes and methods of controlling the delivery of electromagnetic radiation to tissue.

2. Discussion of Related Art

Treatment of certain diseases requires destruction of malignant tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of cancer cells have been found to denature at elevated temperatures that are slightly lower than temperatures normally injurious to healthy cells. Known treatment methods, such as hyperthermia therapy, use electromagnetic radiation to heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator, which functions as an energy source, and a microwave surgical instrument having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

Microwave energy is typically applied via antenna assemblies that can penetrate tissue. Several types of antenna assemblies are known, such as monopole and dipole antenna assemblies. In monopole and dipole antenna assemblies, microwave energy generally radiates perpendicularly away from the axis of the conductor. A monopole antenna assembly includes a single, elongated conductor that transmits microwave energy. A typical dipole antenna assembly has two elongated conductors, which are linearly aligned and positioned end-to-end relative to one another with an electrical insulator placed therebetween. Each conductor may be about ¼ of the length of a wavelength of the microwave energy, making the aggregate length of the two conductors about ½ of the wavelength of the supplied microwave energy.

SUMMARY

According to one embodiment of the present disclosure a microwave ablation system is disclosed. The microwave ablation system includes an energy source adapted to generate microwave energy and a plurality of energy delivery devices having a first energy delivery device configured to be inserted into tissue and to generate a non-directional ablation volume and a second energy delivery device configured to be positioned relative to the tissue and to generate a directional ablation volume. The system also includes a power dividing device having an input adapted to connect to the energy source and a plurality of outputs configured to be coupled to the plurality of energy delivery devices. The power dividing device is configured to selectively divide energy provided from the energy source between the plurality of energy delivery devices.

According to another embodiment of the present disclosure a microwave ablation system is disclosed. The system includes a plurality of energy sources adapted to generate microwave energy and a plurality of energy delivery devices each of which is coupled to a corresponding one of the plurality of energy sources. The plurality of energy delivery devices includes a first energy delivery device configured to be inserted into tissue and to generate a non-directional ablation volume and a second energy delivery device configured to be positioned relative to the tissue and to generate a directional ablation volume.

A method for providing energy to a target tissue is also contemplated by the present disclosure. The method includes the steps of coupling a plurality of energy delivery devices including a non-directional energy delivery device and a directional energy delivery device to a power dividing device having an input adapted to connect to an energy source. The method also includes the steps of inserting the non-directional energy delivery device into a portion of the target tissue and positioning the directional energy device at a surface of the target tissue. The method further includes the steps of selectively dividing energy on a plurality of channels to the plurality of the energy delivery devices and applying energy from the plurality of energy delivery devices to the target tissue.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
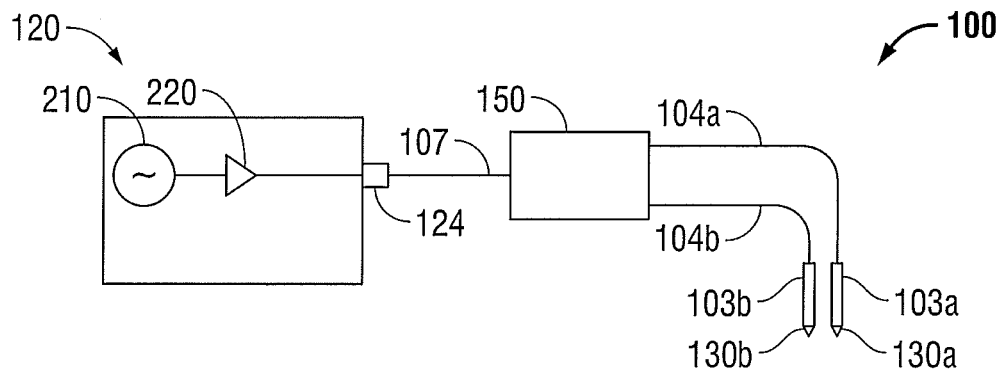
FIGS. 1A-1B is a schematic diagram of an electrosurgical system for treating tissue, according to an embodiment of the present disclosure.

Hereinafter, embodiments of the presently disclosed tissue ablation systems are described with reference to the accompanying drawings. Like reference numerals may refer to similar or identical elements throughout the description of the figures. As used herein, the term "microwave" generally refers to electromagnetic waves in the frequency range of 300 megahertz (MHz) (3×108 cycles/second) to 300 gigahertz (GHz) (3×1011 cycles/second). As used herein, the phrase "transmission line" generally refers to any transmission medium that can be used for the propagation of signals from one point to another. Examples of suitable transmission lines include coaxial cables, waveguides, and combinations thereof.

Various embodiments of the present disclosure provide electrosurgical systems for treating tissue and methods of controlling the delivery of electromagnetic radiation to tissue. Embodiments may be implemented using electromagnetic radiation at microwave frequencies or at other frequencies. Electrosurgical systems for treating tissue, according to various embodiments of the present disclosure, deliver microwave power to a plurality of electrosurgical devices. Electrosurgical devices, such as ablation probes, for implementing embodiments of the present disclosure may be inserted directly into tissue, inserted through a lumen, such as a vein, needle or catheter, placed into the body during surgery by a clinician, or positioned in or on the body by other suitable methods known in the art.

FIG. 1A is a schematic diagram of an electrosurgical system 100 for treating tissue, according to one embodiment of the present disclosure. Referring to FIG. 1A, the electrosurgical system 100 includes an electrosurgical generator 120 for generating an output signal, a power divider 150 coupled to the electrosurgical generator 120, and a plurality of microwave antenna assemblies (e.g., microwave antenna assemblies 130a and 130b) coupled to the power divider 150. The power divider 150 is coupled to a transmission line 107 that electrically connects the power divider 150 to an output 124 on the electrosurgical generator 120. The microwave antenna assemblies 130a and 130b are coupled to transmission lines 104a and 104b that electrically connect the microwave antenna assemblies 130a and 130b to the power divider 150, respectively.

The transmission lines 104a and 104b may be coaxial and may include an inner conductor surrounded by an inner insulator, which is, in turn, surrounded by an outer conductor (e.g., a cylindrical conducting sheath). In one embodiment, the transmission lines 104a and 104b may be formed from a coaxial, semi-rigid or flexible cable having a wire with a 0.047" outer diameter rated for 50 Ohms.

Figure 2A:
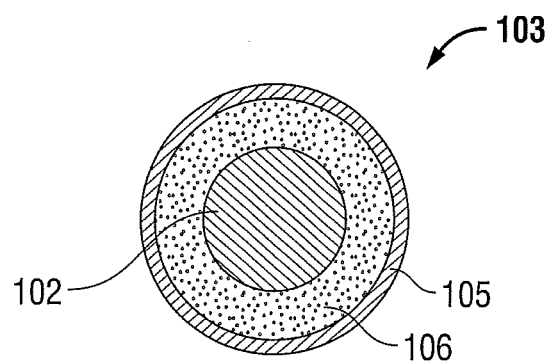
FIGS. 2A-2B are cross-sectional views of a feedline according to the present disclosure.
Figure 2B:
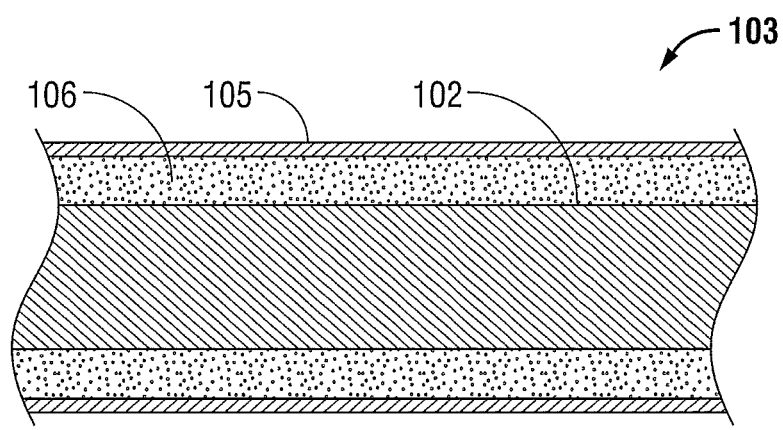

Each of the antenna assemblies 130a and 130b includes feedlines 103a and 103b, respectively. In one embodiment, as seen in FIGS. 2A-2B, feedline 103 (e.g., feedlines 103a and 103b) may be a coaxial cable composed of an inner conductor 102, an outer conductor 105, and an inner insulator 106 interposed between inner and outer conductors 102, 105 to electrically separate and/or isolate inner and outer conductors 102, 105 from one another. Inner and outer conductors 102, 105 may each be made of a suitable conductive material that may be semi-rigid or flexible, while inner insulator 106 may include any number of suitable non-conductive materials such as ceramic and polytetrafluoroethylene (PTFE). Inner and outer conductors 102, 105 of feedline 103 may incorporate any suitable conductive material or metal, including, but not limited to, silver, copper and gold. In certain embodiments, inner and outer conductors 102, 105 of feedline 103 may include a conductive or non-conductive substrate plated or coated with a suitable conductive material. The inner conductor 102 and outer conductor 105 may be constructed of copper, gold, stainless steel or other conductive metals with similar conductivity values.

The electrosurgical generator 120 may include other input or output devices such as knobs, dials, switches, buttons, graphical user interfaces, displays, and the like for control, indication and/or operation. The electrosurgical generator 120 may be capable of generating a plurality of output signals of various frequencies that are input to the power divider 150. In one embodiment, the electrosurgical generator 120 generates a plurality of microwave signals at substantially the same frequency. The electrosurgical generator 120 may include a control unit (not shown) that controls operations of the electrosurgical generator 120, such as time of operation, power output and/or the mode of electrosurgical operation, which may have been selected by the clinician.

The generator 120 includes a microwave signal source 210 that provides a microwave frequency output signal to a microwave amplifier unit 220. The microwave signal source 210 is capable of generating a plurality of output signals of various frequencies that are input to the microwave amplifier unit 220. The microwave amplifier unit 220 may have any suitable input power and output power. In an embodiment, the generator 120 is implemented with operating frequencies in the range of about 300 MHz to about 5 GHz, which may be useful in performing ablation procedures and/or other procedures. It is to be understood that the generator 120 may be implemented with any appropriate range of operating frequencies.

The electrosurgical system 100 may include a footswitch (not shown) coupled to the electrosurgical generator 120. When actuated, the footswitch causes the electrosurgical generator 120 to generate microwave energy. The microwave antenna assemblies 130a and 130b may include knobs, dials, switches, buttons or the like (not shown) to communicate to the electrosurgical generator 120 to adjust or select from a number of configuration options for delivering energy. Utilizing knobs, dials, switches or buttons on the microwave antenna assemblies 130a and 130b and/or a footswitch enables the clinician to activate the electrosurgical generator 120 to energize the microwave antenna assemblies 130a and 130b while remaining near a patient regardless of the location of the electrosurgical generator 120.

Although not shown as such in FIG. 1A, electrosurgical system 100 may include a plurality of channels defined by a plurality of electrosurgical devices and a plurality of transmission lines that electrically connect the electrosurgical devices to the power divider 150. In an embodiment, the power divider 150 is capable of monitoring the phase of each channel and adjusting the phase of the signal in each channel with respect to the other channel(s) to a predetermined phase relationship. The power divider 150 provides a plurality of signals to the microwave antenna assemblies 130a and 130b in a set of phase relationships between the signals. Although the power divider 150 is illustrated as a standalone module in FIG. 1A, it is to be understood that the power divider 150 may be integrated fully or partially into the electrosurgical generator 120, the microwave antenna assemblies 130a and 130b, and/or other devices.

In another embodiment, the power divider 150 may be a power splitter configured to split an input signal from the electrosurgical generator 120 into two or more equal phase output signals, such as a Wilkinson power splitter. The power divider 150 may be implemented by any suitable power divider that provides equal or unequal power split at the output ports of the microwave power divider 150 while substantially maintaining phase and amplitude balance. For example, the microwave power divider 150 may be implemented using a 2-way power divider that provides equal or unequal power split at its output ports while maintaining a phase balance of less than ±45 degrees. Various embodiments of the power divider 150 are described in a commonly-owned U.S. application Ser. No. 12/562,842 entitled "Tissue Ablation System With Energy Distribution," the entire disclosure of which is incorporated by reference herein.

Figure 1B:
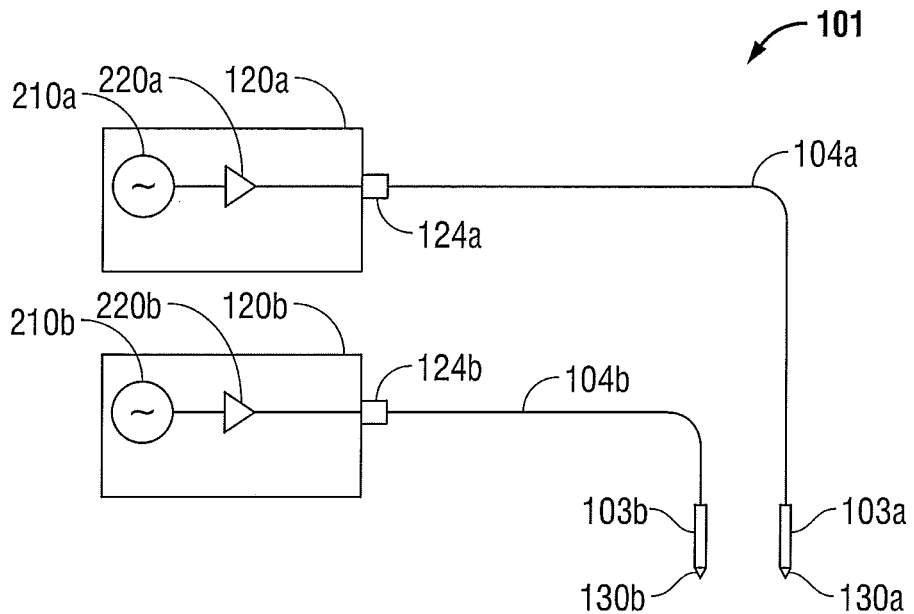

FIG. 1B shows another embodiment of an electrosurgical system 101 for treating tissue. Referring to FIG. 1B, the electrosurgical system 101 includes a plurality of electrosurgical generators (e.g., electrosurgical generators 120a and 120b) for generating an output signal, and a plurality of microwave antenna assemblies (e.g., microwave antenna assemblies 130a and 130b). The microwave antenna assemblies 130a and 130b are coupled to transmission lines 104a and 104b that electrically connect the microwave antenna assemblies 130a and 130b to outputs 124a and 124b of the electrosurgical generators 120a and 120b, respectively.

The electrosurgical generators 120a and 120b are substantially similar to the electrosurgical generator 120 of the system 100. Each of the generators 120a and 120b includes microwave signal sources 210a and 210b for providing a microwave frequency output signal to microwave amplifier units 220a and 220b, respectively. The system 101 pairs each of the electrosurgical generators 120a and 120b with each of the corresponding microwave antenna assemblies 130a and 130b, thereby obviating the need for the power divider 150 of the system 100. Each of the generators 120a and 120b may be configured to equal or unequal power while substantially maintaining phase and amplitude balance therebetween.

Figure 5:
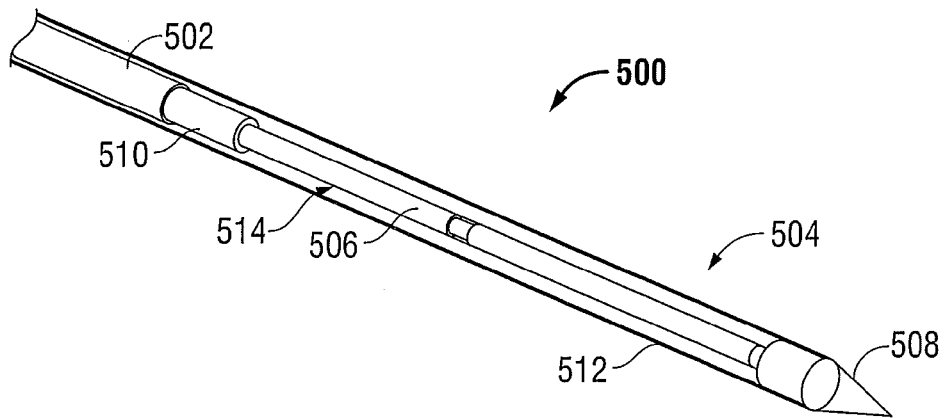
FIG. 5 perspective, cross-sectional view of further embodiment of a microwave antenna assembly according to the present disclosure.

In some embodiments, one of the microwave antenna assemblies 130a and 130b may be a microwave antenna configured to allow direct insertion or penetration into tissue. The microwave antenna assemblies 130a and 130b may be axially rigid to allow for tissue penetration either directly into tissue or inserted through a lumen, such as, for example, a vein, needle or catheter, or otherwise positioned in the body by other suitable methods as shown in FIG. 5.

Figure 3:
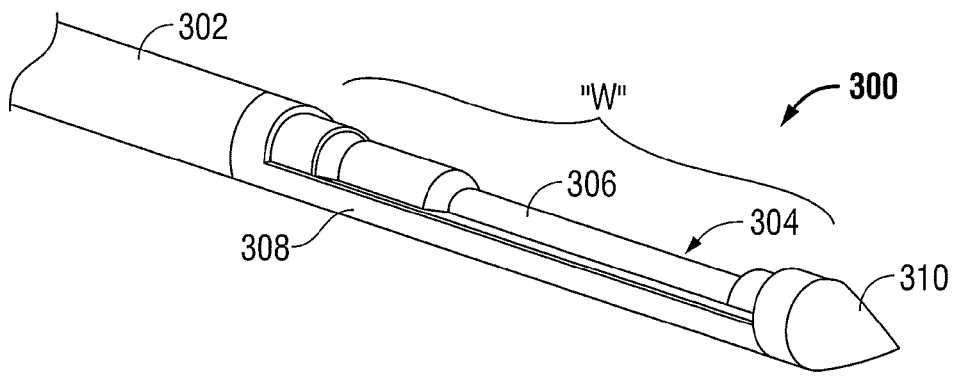
FIG. 3 is a perspective, cross-sectional view of a microwave antenna assembly according to the present disclosure.
Figure 4:
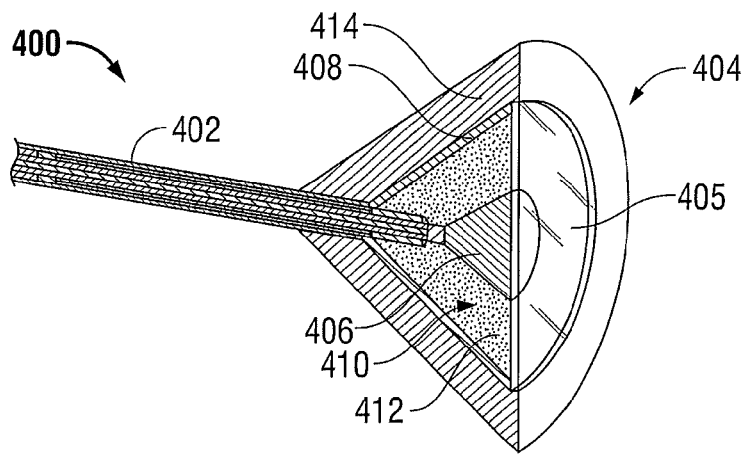
FIG. 4 is a perspective, cross-sectional view of another embodiment of a microwave antenna assembly according to the present disclosure.

In another embodiment, one of the microwave antenna assemblies 130a and 130b may be a so-called "window" microwave antenna suitable for directing microwave energy in a predetermined direction as shown in FIG. 3. In a further embodiment, one of the microwave antenna assemblies 130a and 130b may be a surface microwave waveguide for directing microwave energy through the tissue surface as shown in FIG. 4.

Although the electrosurgical systems 100 and 101 illustrated in FIGS. 1A and 1B include two microwave antenna assemblies 130a and 130b, it is to be understood that any "N" number of antenna assemblies may be utilized. The microwave power divider 150 may be implemented by any suitable power divider that divides or splits a microwave input signal into "N" number of output signals of equal or unequal power.

By controlling the phase of ablation probes with respect to each other, according to embodiments of the present disclosure, a desired effect on tissue between the probes is produced. In a resection procedure where a long thin ablation line may be desired, probes that are 180 degrees out of phase with respect to each other produce a desired effect on tissue. In ablation procedures using in-phase probes, according to various embodiments of the present disclosure, there may be a reduction in energy that might otherwise move between the antenna shafts toward the surface with out-of-phase probes. Otherwise, the generators 120a and 120b may be configured in a similar manner.

In another embodiment, the electrosurgical systems 100 and 101 (e.g., either through the power splitter 150 or through multiple generators 120a and 120b) deliver microwave power to particular channels individually or any combination of one or more channels equally or unequally to facilitate selective activation of energy delivery to particular channels or combination of channels. For example, a user may select channels to which energy is delivered. In this scenario, if the second and third channels are selected, energy delivery may be divided equally (e.g., P/2) between the second and third channels and, thus, unequally between the first channel and the second and third channels since no energy is delivered to the first channel in this scenario. Further, in this scenario, energy may be delivered to individual channels according to selected time intervals by dynamically changing the channels to which energy is delivered. For example, energy may be delivered to the first channel at a time interval t1. At a subsequent time interval t2, energy is delivered to the first channel and the third channel. At a subsequent time interval t3, energy delivery to the first channel is stopped and energy delivery to the third channel continues. At a subsequent time interval t4, energy delivery to all channels is stopped.

In another embodiment, the microwave power divider 150 and/or the generators 120a and 120b may divide energy between the antenna assemblies 130a and 130b to tailor the size and shape of ablation lesions. With this purpose in mind, generators 120, 120a and 120b may include a suitable storage device (not shown) integrated therein that is configured to store settings or data corresponding to particular ablation geometries (e.g., ablation images, antenna tip geometries, power division settings, power amplitude settings, etc.). Based on the stored settings or data, the generators 120a and 120b modify delivery of microwave power and/or the microwave power divider 150 modifies the division of microwave power between the channels to achieve the desired ablation geometry.

FIG. 3 shows an antenna assembly 300 according to one embodiment of the present disclosure. The antenna assembly 300 includes a feedline 302 that is coupled to one of the transmission lines 104a and 104b. The antenna assembly 300 includes a radiating section 304 including a dipole antenna 306. The antenna assembly 300 also includes a dielectric shield 308 disposed about a portion of the dipole antenna 306 along the entire length thereof. In one embodiment, the dielectric shield 308 may have a substantially half-cylindrical shape (e.g., 180°). In another embodiment, the dielectric shield 308 may be made to encompass any radial angle. The antenna assembly 300 also includes a tip 310 having a tapered portion terminating in a sharp tip to allow for insertion into tissue with minimal resistance. In those cases where the energy applicator is inserted into a pre-existing opening, the tip 310 may be rounded or flat.

The dielectric shield 308 and the tip 310 may be formed from a suitable polymeric material, which may include, for example, thermoplastics including reinforced or unreinforced polymers, e.g., polyamide (nylon) or polyaramid (e.g., KEVLAR® manufactured by E. I. du Pont de Nemours and Company of Wilmington, Del., United States), or any suitable polymeric composite, e.g., polymers filled with carbon particles, silica, conductive particles such as metal particles or conductive polymers, or combinations thereof.

The dielectric shield 308 forms an opening or electromagnetic "window" shown generally as "W" partially defined by the longitudinal edges of the dielectric shield 308. The dielectric material of the dielectric shield 308 limits the transmission of the microwave energy therethrough, which directs the microwave energy through the window "W." This configuration allows for the antenna assembly to be used to generate non-spherical and directed ablation volumes. The antenna assembly 300 is a so-called "directional" antenna since the radiating section 304 is configured to emit microwave energy in a specific direction. Various embodiments of windowed microwave antenna assemblies are described in a commonly-owned U.S. application Ser. No. 12/535,856 entitled "Directive Window Ablation Antenna With Dielectric Loading," the entire disclosure of which is incorporated by reference herein.

FIG. 4 shows a waveguide antenna assembly 400 according to one embodiment of the present disclosure. The antenna assembly 400 includes a feedline 402 that is coupled to one of the transmission lines 104a and 104b. The antenna assembly 400 includes a waveguide section 404 having a radiating cone 406 and a conical reflector 408 coupled to the inner and outer conductors of the feedline 402, respectively. The radiating cone 406 and the conical reflector 408 have a generally conical shape having a truncation at a proximal apex end and are dimensioned to couple to a distal end of the feedline 402, with the conical reflector disposed over the radiating cone 406. The antenna assembly 400 also includes a dielectric shield 414 disposed on the outer surface of the conical reflector 408 along the entire length thereof.

The antenna assembly 400 includes a membrane 405 that is disposed between the radiating cone 406 and the conical reflector 408, which define a chamber 410 therebetween having a corresponding conical shape. Membrane 405 may be formed of any suitable radiofrequency-transparent material of low electrical conductivity, e.g., material that enables efficient transmissivity of microwave ablation signals to tissue from the energy delivery system, including without limitation, the conical radiating structure herein described. Membrane 405 may be formed from a rigid material, or may be formed from flexible and/or elastomeric material. The antenna assembly 400 is a so-called "directional" antenna since the waveguide section 404 is configured to emit microwave energy in a specific direction.

The lumen 410 is filled with a dielectric material 412 which may be a dielectric fluid circulated therethrough or any type of suitable solid dielectric. The dielectric material 412 and the dielectric shield 414 may be formed from a suitable dielectric material similar to the material as the dielectric shield 308.

The antenna assembly 400 is configured for surface transmission of microwave energy. In use, the antenna assembly 400 is disposed on a surface of the tissue with the surface with the membrane 405 contacting the tissue. The microwave energy applied to the antenna assembly 400 is directed by the waveguide section 404 into the tissue through the surface thereof. Various embodiments of a conical microwave antenna assemblies are described in a commonly-owned U.S. application Ser. No. 12/568,551 entitled "Microwave Surface Ablation Using Conical Probe," the entire disclosure of which is incorporated by reference herein.

FIG. 5 shows an antenna assembly 500 according to one embodiment of the present disclosure. The antenna assembly 500 includes a feedline 502 that is coupled to one of the transmission lines 104a and 104b. The antenna assembly 500 includes a radiating section 504 including a dipole antenna 506. The antenna assembly 500 also includes a tip 508 having a tapered portion terminating in a sharp tip to allow for insertion into tissue with minimal resistance. In those cases where the energy applicator is inserted into a pre-existing opening, the tip 508 may be rounded or flat. The antenna assembly 500 is a so-called "non-directional" antenna since the radiating section 504 radiates microwave energy in all directions resulting in an ablation volume that is symmetrical about a longitudinal axis defined by the antenna assembly 500.

In one embodiment, the antenna assembly 500 may include a choke 510 and a sheath 512 enclosing the dipole antenna 506. The sheath 512 defines a chamber 514 that may be filled with a suitable dielectric material (e.g., liquid or solid loading). In use, the antenna assembly 500 is inserted into tissue and upon application of microwave energy generates substantially spherical ablation volumes based on the dielectric loading about the dipole antenna 506. Various embodiments of a choked dielectric loaded microwave antenna assemblies are described in a commonly-owned U.S. Provisional Application Ser. No. 61/023,031 entitled "Choked Dielectric Loaded Tip Dipole Microwave Antenna," the entire disclosure of which is incorporated by reference herein.

Figure 6:
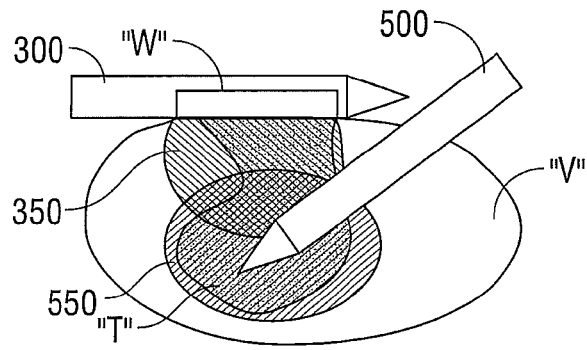
FIG. 6 is a cross-sectional view of multiple microwave antenna disposed in tissue assemblies according to the present disclosure.
Figure 7:
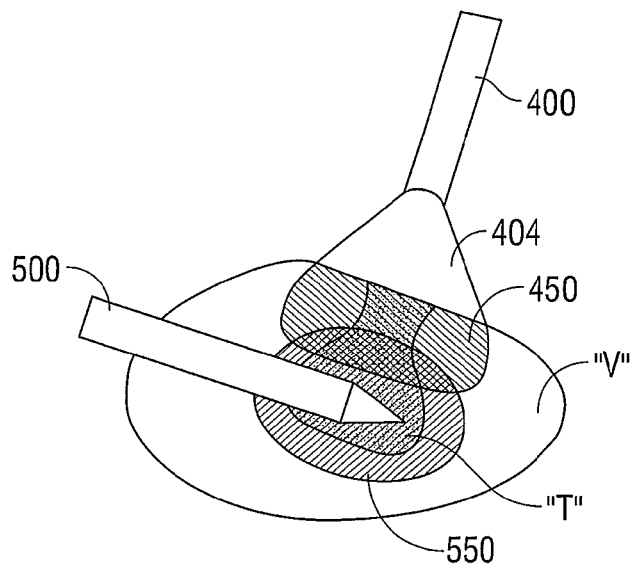
FIG. 7 is a cross-sectional view of multiple microwave antenna disposed in tissue assemblies according to the present disclosure.
Figure 8:
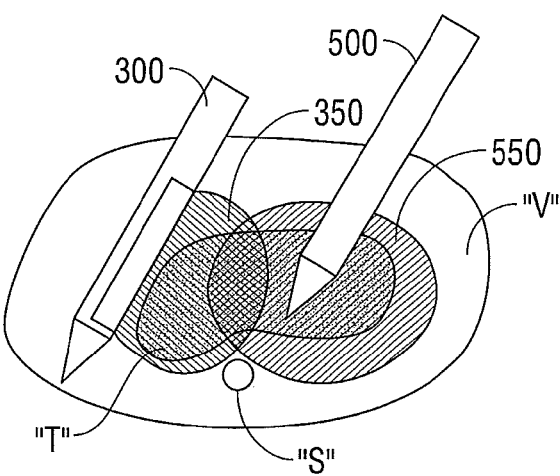
FIG. 8 is a cross-sectional view of multiple microwave antenna disposed in tissue assemblies according to the present disclosure.

FIGS. 6-8 illustrate various embodiments of using a plurality of antenna assemblies 130a and 130b to ablate tissue. In particular, the present disclosure provides for systems and methods for performing microwave ablation with internal and external radiation sources simultaneously by connecting the antenna assemblies 130a and 130b to a single generator 120 or each of the antenna assemblies 130a and 130b to a corresponding generator 120a and 120b.

In use, the antenna assembly 500 is inserted into tissue and is placed directly through the center of a target tissue volume (e.g., tumor). Once energized, the antenna assembly 500 produces a symmetrical ablation volume (e.g., oval or sphere-shaped) about a longitudinal axis defined by the antenna assembly 500. In certain situations, a symmetrical ablation volume is not well suited for ablating a non-spherical tumor. More specifically, the antenna assembly 500 is not suited for ablating the entire tumor having an irregular shape without destroying a significant portion of healthy tissue. Utilizing additional antenna assemblies 500 is not efficient either, since overlapping of the symmetrical ablation volume may not closely approximate the tumor. In this situation, using directional microwave antennas (e.g., external antenna assemblies 400 or windowed antenna assemblies 300) in conjunction with non-directional antennas (e.g., the antenna assembly 500) provides for an optimal configuration of the ablation volume with respect to the tumor. In other words, combination of antenna assemblies 300, 400, 500 allows for generation of ablation volumes having highest conformation parameters for encompassing irregularly shaped tumors.

FIG. 6 illustrates the use of the antenna assembly 300 and the antenna assembly 500 to ablate a tumor "T" that is partially disposed at the surface of a tissue volume "V." The antenna assembly 500 is inserted through a larger portion of the tumor "T," such that an ablation volume 550 encompasses the larger portion of the tumor "T." The antenna assembly 300 is disposed on the surface of the tissue volume "V" such that the window "W" is facing a portion of the tumor "T." The antenna assembly 300 generates an ablation volume 350 just beyond the surface of the tissue volume "V." The ablation volume 350 overlaps with the ablation volume 550, but also encompasses the portion of the tumor "T" that is outside of the ablation volume 550.

FIG. 7 illustrates the use of the antenna assembly 400 and the antenna assembly 500 to ablate the tumor "T" that is partially disposed at the surface of the tissue volume "V." The antenna assembly 500 is inserted through a larger portion of the tumor "T," such that an ablation volume 550 encompasses the larger portion of the tumor "T." The antenna assembly 400 is disposed on the surface of the tissue volume "V" such that the waveguide section 404 is facing a portion of the tumor "T." The antenna assembly 400 generates an ablation volume 450 just beyond the surface of the tissue volume "V." The ablation volume 450 overlaps with the ablation volume 550, but also encompasses the portion of the tumor "T" that is outside of the ablation volume 550.

FIG. 8 illustrates the use of the antenna assembly 300 and the antenna assembly 500 to ablate a tumor "T" that is disposed within tissue volume "V." The antenna assembly 500 is inserted through a larger portion of the tumor "T," such that an ablation volume 550 encompasses the larger portion of the tumor "T." The antenna assembly 300 is also inserted into the tissue volume "V" such that the window "W" is facing a portion of the tumor "T." The antenna assembly 300 generates an ablation volume 350 that overlaps with the ablation volume 550, but also encompasses the portion of the tumor "T" that is outside of the ablation volume 550.

Collateral damage to healthy tissue is reduced by matching the shape of the tumor "T" to the ablation volumes 350, 450, 550 instead of creating a spherical volume large enough to cover the abnormally-shaped tumor "T." In addition, as shown in FIG. 8, the antenna assemblies 300 and 500 may be positioned within the tissue volume "V" to avoid ablation of critical structures "S" (e.g., blood vessels). The directional radiation of antenna assemblies 300 and 400 supplement the non-directional radiation of the antenna assembly 500, allowing for the achievement of the desired ablation boundaries. In addition, internal antennas (e.g., antenna assemblies 300 and 500) may ablate deeper tissues, while the external antennas (e.g., antenna assemblies 300 and 400) may ablate surface tissues.

Figure 9:
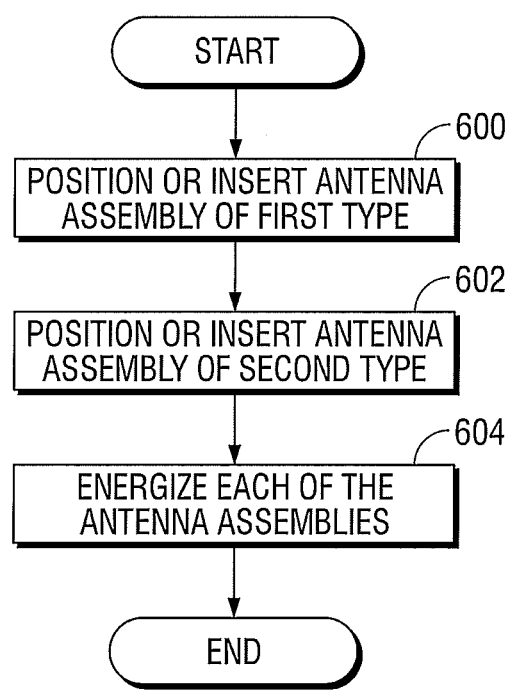
FIG. 9 is a block diagram illustrating a method for treating tissue, according to an embodiment of the present disclosure.

FIG. 9 illustrates a flow chart of a method according to the present disclosure. In step 600, the antenna assembly 130a (e.g., antenna assembly 500) is inserted into the tissue volume "V." In step 602, the antenna assembly 130b (e.g., antenna assembly 300 or 400) is positioned or otherwise inserted into the tissue volume "V." The antenna assemblies 130a and 130b are positioned such that the ablation volumes conform to the volume of the tumor "T" while avoiding encompassing any of the critical structures "S." In another embodiment, multiple antenna assemblies 103 and 130b (e.g., two antenna assemblies 500 and a single antenna assembly 300) may be used to obtain various ablation volumes. Each of the antenna assemblies 130a and 130b is coupled to a single generator 120 via the power divider 150 or to a corresponding generator 120a and 120b. In step 604, each of the antenna assemblies 130a and 130b is energized simultaneously to generate a combined ablation volume.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A microwave ablation system, comprising:
an energy source adapted to generate microwave energy;
a first energy delivery device configured to be inserted into tissue and to emit microwave energy in a plurality of directions to generate a non-directional ablation volume that is symmetrical about a longitudinal axis defined by the first energy delivery device;
a second energy delivery device configured to be positioned relative to tissue and to emit microwave energy in a specific direction to generate a directional ablation volume that is non-spherical, wherein the second energy delivery device includes:
a feedline including an inner conductor, an outer conductor, and an inner insulator disposed between the inner and outer conductors;
a waveguide section coupled to the feedline and including a radiating cone and a conical reflector; and
a membrane disposed between the radiating cone and the conical reflector; and
a power dividing device including:
an input adapted to connect to the energy source;
a first output configured to be coupled to the first energy delivery device; and
a second output configured to be coupled to the second energy delivery device, the power dividing device configured to selectively divide energy provided from the energy source between the first and second energy delivery devices.

2. A microwave ablation system according to claim 1, wherein the radiating cone is coupled to the inner conductor and the conical reflector is coupled to the outer conductor.

3. A microwave ablation system according to claim 1, wherein the conical reflector is disposed over the radiating cone.

4. A microwave ablation system according to claim 1, wherein the waveguide section further includes a dielectric shield disposed on an outer surface of the conical reflector and along a length of the conical reflector.

5. A microwave ablation system according to claim 1, wherein the membrane is formed of a radiofrequency-transparent material.

6. A microwave ablation system according to claim 1, wherein the waveguide section includes a dielectric material disposed between the radiating cone and the conical reflector.

7. A microwave ablation system, comprising:
an energy source adapted to generate microwave energy;
a first energy delivery device configured to be inserted into tissue and to emit microwave energy in a plurality of directions to generate a non-directional ablation volume that is symmetrical about a longitudinal axis defined by the first energy delivery device;
a second energy delivery device configured to be positioned relative to tissue and to emit microwave energy in a specific direction to generate a directional ablation volume that is non-spherical, wherein the second energy delivery device includes:
a feedline including an inner conductor, an outer conductor, and an inner insulator disposed between the inner and outer conductors;
a waveguide section coupled to the feedline and including a radiating cone and a conical reflector; and
a dielectric material disposed between the radiating cone and the conical reflector; and a power dividing device including:
- an input adapted to connect to the energy source;
- a first output configured to be coupled to the first energy delivery device; and
- a second output configured to be coupled to the second energy delivery device, the power dividing device configured to selectively divide energy provided from the energy source between the first and second energy delivery devices.

* * * * *